United States Patent [19]

Cordier

[11] Patent Number: 4,533,771

[45] Date of Patent: Aug. 6, 1985

[54] PROCESS FOR THE PREPARATION OF TRIFLUOROETHANOL

[75] Inventor: Georges Cordier, Francheville, France

[73] Assignee: Rhone-Poulenc Specialites Chimiques, Courbevoie, France

[21] Appl. No.: 596,938

[22] Filed: Apr. 5, 1984

[30] Foreign Application Priority Data

Apr. 21, 1983 [FR] France ............................... 83 06530

[51] Int. Cl.$^3$ ..................... C07C 29/136; C07C 31/38
[52] U.S. Cl. .................................................... 568/842
[58] Field of Search ......................................... 568/842

[56] References Cited

U.S. PATENT DOCUMENTS

| | | | |
|---|---|---|---|
| 2,750,263 | 6/1956 | De Nora et al. | 568/864 |
| 2,862,977 | 12/1958 | Schreyer | 568/842 |
| 3,180,898 | 4/1965 | Eisenlohr et al. | 568/885 |
| 3,663,629 | 5/1972 | Fischer | 568/842 |
| 4,273,947 | 6/1981 | Novotny | 568/842 |
| 4,396,784 | 8/1983 | Johnson et al. | 568/842 |

FOREIGN PATENT DOCUMENTS 7031913   6/1971   France .

Primary Examiner—J. E. Evans
Attorney, Agent, or Firm—Finnegan, Henderson, Farabow, Garrett & Dunner

[57] ABSTRACT

Process for the preparation of trifluoroethanol by the hydrogenation of trifluoroacetic acid in the liquid phase. The reaction is carried out in the presence of a catalyst based on ruthenium, rhodium, iridium or platinum, under a total pressure of between 5 and 50 bar, and with a ratio of the volume of the liquid phase used in the reactor to the total volume of the reactor of more than about $\frac{1}{2}$. An absolute partial pressure of hydrogen of more than 1 bar is maintained during the reaction.

18 Claims, No Drawings

PROCESS FOR THE PREPARATION OF TRIFLUOROETHANOL

The present invention relates to a process for the preparation of trifluoroethanol; it relates more particularly to a process for the preparation of trifluoroethanol from trifluoroacetic acid.

French Patent Application 70/31,913, published under No. 2,060,357, is known in the prior art and describes the preparation of 1,1-dihydroperfluoroalkanols corresponding to the general formula $C_nF_{2n+1}CH_2OH$, in which $n \geq 3$, by the hydrogenation of acids or esters of the formula $C_nF_{2n+1}COOR$, in which R represents a hydrogen atom or an alkyl radical and in which $n \geq 3$, in the presence of a ruthenium-based catalyst.

In this process, the hydrogenation is carried out in the presence of 4 to 1000% by weight of water, relative to the acid or ester, and under a high temperature and a high hydrogen pressure. The temperature is between 80° and 240° C. and the initial hydrogen pressure varies between 5 and 700 kgp/cm$^2$.

This process makes no provision for the possibility of using trifluoroacetic acid (n=1) to obtain trifluoroethanol.

The preparation of trifluoroethanol is again not envisaged in U.S. Pat. No. 2,862,977, which describes the preparation of 1,1-dihydroperfluoroalkylalcohols of the formula $C_nF_{2n+1}CH_2OH$ (n>1) by the hydrogenation of the corresponding acid under a pressure of at least 1000 p.s.i. (70 bar) and at a temperature above 150° C., in the presence of a ruthenium-based catalyst.

U.S. Pat. No. 4,273,947 is also known, which describes a process for the hydrogenation of trifluoroacetic acid (CF$_3$COOH) in which this acid is brought into contact with hydrogen in the liquid phase, in the presence of a supported or unsupported catalyst based on rhodium or iridium, under a pressure of 5 to 15 atmospheres and at a temperature of 50° to 150° C.

Examples 1 to 9 of the said U.S. patent show that, in a reaction enclosure having a volume of 0.206 liter, very small quantities of trifluoroacetic acid are used (from 1.9 to 3.31 g). This corresponds to a ratio of the volume of liquid used to the volume of the reaction enclosure of between about 0.007 and about 0.015 (Example 10 relates to a vapour-phase process). It is clear to those skilled in the art that these conditions are incompatible with a viable industrial operation.

By studying the processes of the prior art which have been analysed above, the inventor has found that, in the case of the hydrogenation of trifluoroacetic acid, secondary hydrogenolysis reactions develop, giving rise to gaseous products such as HF, CF$_3$-CH$_3$, CH$_3$-CH$_3$ and CH$_4$, which accumulate in the reactor and block the hydrogenation reaction. These secondary reactions also exist in the case of acids having a larger number of carbon atoms, but, in this case, the by-products have a much lower vapor pressure and do not have such an adverse effect on the hydrogenation reaction. The inventor has furthermore found that these secondary reactions are more significant in the case of a ruthenium-based catalyst than in the case of a rhodium-based catalyst.

The inventor has discovered that, on the one hand, these secondary reactions develop during the hydrogenation reaction and that, on the other hand, because of the production of these inert gases at constant total pressure, they reduce the hydrogen partial pressure until the main reaction stops.

The inventor has furthermore found that, to be able to hydrogenate trifluoroacetic acid in the presence of a ruthenium-based catalyst, it would be necessary to apply a high pressure and to use a large reaction volume so that the gaseous by-products do not affect the reaction. These two conditions detract very greatly from the economics of an industrial process.

In the presence of a rhodium-based catalyst, the reaction must be carried out either under high pressure or under low pressure, in which case, however, it must be carried out in a large reaction volume as pointed out above in the analysis of the process of the prior art described in U.S. Pat. No. 4,273,947. This condition relating to the reactor makes this process incompatible with an industrial-scale operation, in which the reaction is generally carried out with a ratio of the volume of liquid used to the total volume of the reactor of more than about 0.5.

The inventor has now discovered a process making it possible to carry out the reaction under low pressure and at the same time under satisfactory conditions of reaction volume.

The invention therefore relates to a process for the preparation of trifluoroethanol by the hydrogenation of trifluoroacetic acid in the liquid phase, which comprises carrying out the reaction in the presence of a catalyst based on ruthenium, rhodium, iridium or platinum, under a total pressure of between 5 and 50 bar, with a ratio of the volume of the liquid phase used in the reactor to the total volume of the reactor of more than about $\frac{1}{2}$, and maintaining an absolute partial pressure of hydrogen of more than 1 bar during the reaction.

In one particular embodiment of the invention, the absolute partial pressure of hydrogen is maintained at a value of more than 1 bar by allowing some of the gas phase present in the reactor to escape continuously during the reaction.

As a consequence of what has been stated above, the invention is more particularly advantageous when operating in a total pressure range of between 5 and 30 bar.

In another preferred embodiment of the invention, the reaction is carried out by charging the reactor so as to correspond to a ratio of the volume of the liquid phase to the total volume of the reactor of between 0.5 and 0.8.

According to another preferred embodiment of the invention, the hydrogen partial pressure is maintained at a value of more than 5 bar. From these teachings, it will be clear to those skilled in the art that the lower the total pressure and the higher the hydrogen partial pressure, the faster the reaction will be. A compromise between these two tendencies will easily be found by those skilled in the art, taking account of the technological and economic constraints with which they will be faced.

The catalysts used within the scope of the process according to the invention can be in the form of the metal itself or in the form of an oxide or a salt, or a mixture of these. Furthermore, they may or may not be deposited on a support.

It is possible to use any support which is inert under the reaction conditions, such as charcoal, silica or alumina. The use of charcoal will be very particularly preferred.

The quantity of metal deposited on the support is preferably between 0.1 and 20% by weight and more preferably between 1 and 10%.

Examples of catalysts which may be mentioned are: ruthenium, rhodium, iridium or platinum in the form of the metal, their oxides, hydroxides and salts with acids (halides, nitrates, sulfates and acetates) and mixtures of these, if appropriate deposited on charcoal or silica.

In a very particularly preferred embodiment, rhodium metal deposited in a proportion of 5% on charcoal is used.

The reaction is preferably carried out at a temperature of between 20° and 200°. Even more preferably, the temperature is between 70° and 150° C.

The quantity of catalyst used (expressed in % of the metal) is preferably less than 10% by weight, relative to the trifluoroacetic acid. Even more preferably, less than 2% of catalyst is used.

The reaction preferably takes place in the presence of a solvent. However, it is not excluded to carry out the reaction without a solvent. Water or an inert organic compound (for example an alkane) can be used. Water facilitates the use of catalysts which are generally sold moist.

Other advantages and characteristics of the invention will become apparent on reading the examples which follow:

EXAMPLE 1

The following are introduced into a corrosion-resistant Hastelloy $B_2$ autoclave having a useful volume of 300 ml and equipped with a turbine stirrer:
25 g of distilled water
3.9 g of a catalyst consisting of rhodium deposited in a proportion of 5% on a charcoal of large specific surface area (>900 m$^2$/g)
298 g, i.e. 2.61 mol, of trifluoroacetic acid.

After the air has been removed by means of an inert gas such as nitrogen, and the latter then replaced with hydrogen, the pressure of the reactor is brought to 28 bar, still with hydrogen, and the reactor is heated to 90° C. The reaction starts while the temperature is rising and the consumption of hydrogen thus compensates for the pressure increase associated with the expansion of the gases. The hydrogen necessary for the reaction is then fed in continuously, the total pressure being maintained at 28 bar.

When the temperature reaches 90° C., the total pressure being maintained at 28 bar by feeding in hydrogen, the gas cover is purged continuously. The purged gas is cooled to 13°–15° C. in a condenser after it has been removed from the reactor.

This purge makes it possible to remove compounds which are uncondensable at this temperature, and by-products of the reaction (essentially methane, ethane and trifluoroethane).

The flow rate of the purge is set at 2.7 liters.h$^{-1}$ (NTP), which, taking account of the reaction time, represents about 10% of the total quantity of hydrogen necessary for the reaction.

The reaction stops after 4 hours 10 minutes.

After the enclosure has been cooled and degassed, analysis of the reaction mixture by VPC shows that the degree of conversion of the trifluoroacetic acid is 97.5%; the yield of trifluoroethanol is 97.5% and that of the volatile by-products defined above is 2.5%.

The solution is then neutralized with the appropriate quantity of sodium hydroxide and filtered, and the filtrate is distilled under atmospheric pressure in order to separate the TFE from the water and the inorganic salts resulting from the neutralization.

The catalyst used in this way could be recycled 3 times without any apparent loss of activity.

EXAMPLE 2

The following are introduced into an enamelled steel autoclave having a useful volume of 4 liters:
37.5 g of a catalyst consisting of rhodium deposited in a proportion of 5% on a charcoal of large specific surface area
300 g of distilled water
2,850 g, i.e. 25 mol, of trifluoroacetic acid.

The procedure of Example 1 is then followed, except that the total pressure in the enclosure is maintained at 10 bar.

When the temperature reaches 90° C., and throughout the whole of the reaction, the gas cover is continuously purged, the total pressure in the enclosure being maintained at 10 bar. The purged gas, after being removed from the reactor, is cooled to 13°–15° C. in a condenser.

The flow rate (NTP) of this purge is 5.5 liters.h$^{-1}$, which represents about 11% of the total quantity of hydrogen necessary to convert the TFA to TFE.

The reaction stops after 22 hours 30 minutes. The analyses and operations described in Example 1 are then repeated.

The degree of conversion of the TFA is 99.3%; the yield (Y) of TFE is 95.7%, the yield of trifluoroethane is 4% and only traces of ethane and methane are found.

EXAMPLE 3

Example 1 is repeated, the following being introduced:
8.8 g of the 5% rhodium catalyst described above
25 g of water
251 g of trifluoroacetic acid (TFA), i.e. 2.2 mol.

The reaction is carried out at 90° C. under a total pressure of 10 bar and 0.25 liter.h$^{-1}$ (NTP) is purged continuously, i.e. a total quantity of gas cover corresponding to about 1% of the total quantity of hydrogen necessary to accomplish the reaction.

The reaction stops after 4 hours 10 minutes.

The degree of conversion of the trifluoroacetic acid is 100%.

The yield (Y) of trifluoroethanol (TFE) is 99%. 1% of compounds resulting from hydrogenolysis ($CF_3CH_3$, $C_2H_6$, $CH_4$) have been formed.

EXAMPLE 4

The reaction is carried out in the same reactor as that described in Example 1. The following are introduced:
26 g of a catalyst consisting of 5% of ruthenium deposited on a charcoal of large specific surface area (>900 m$^2$/g)
70 g of water
179 g (1.57 mol) of TFA.

The reaction is performed, as in Example 1, at 90° C. and under a total pressure of 28 bar.

The flow rate of the purge is set at 1.0 liter.h$^{-1}$ (NTP), i.e. about 16% of the quantity of hydrogen necessary for the reaction.

The reaction stops after 11 hours 30 minutes.

The degree of conversion of the TFA is 96.2%.

The yield (Y) of TFE is 93.5% and that of CF$_3$CH$_3$ is 6.4%. 0.3% of CH$_4$ and 0.06% of ethane are also formed.

EXAMPLE 5

The following are introduced into a 40 ml autoclave resistant to corrosion by trifluoroacetic acid:
4 g of a 5% ruthenium catalyst (cf. Example 3)
22.8 g (0.2 mol) of TFA.

The oxygen and nitrogen are removed in the manner stated in Example 1 and the autoclave is then placed under a hydrogen pressure of 40 bar. The reactor is heated to 150° C.

The pressure is 45 bar at 150° C. It is kept constant throughout the whole of the reaction.

The gas cover is purged continuously in the manner stated in Example 1. This purge represents about 10% of the total quantity of hydrogen necessary to accomplish the reaction.

The reaction stops after 1 hour. The degree of conversion of the TFA is 100%. The yield of TFE is 95.5%. 3.5% of CF$_3$CH$_3$, 0.6% of ethane and 0.4% of methane have also been formed.

EXAMPLE 6

Example 5 is repeated in the same reactor, the following being introduced:

| Ru/C containing 5% of Ru | 2.5 g |
|---|---|
| Water | 7.5 g |
| TFA | 22.8 g (0.2 mol). |

The autoclave is placed under a hydrogen pressure of 50 bar and heated to 90° C. The pressure is kept constant at 50 bar and about 10% of the flow rate of hydrogen fed in is used for continuous purging.

The reaction stops after 4 hours 10 minutes.

The degree of conversion of the TFA is 100%.

The yield (Y) of TFE is 92%. The following are additionally formed:

| CF$_3$CH$_3$ | 7.2% |
|---|---|
| C$_2$H$_6$ | 0.5% |
| CH$_4$ | 0.2% |

EXAMPLE 7

The reaction is carried out as in Example 5, the following being introduced:

| Ruthenium oxide (unsupported) | 2 g |
|---|---|
| Water | 6 ml |
| Trifluoroacetic acid | 22.8 g (0.2 mol). |

The reaction is carried out at 150° C. and under a total pressure of 50 bar, about 12% of the total quantity of hydrogen fed in being used for continuous purging.

The reaction stops after 1 hour 40 minutes.

The degree of conversion of the trifluoroacetic acid is 100%; the yield (Y) of TFE is 86.9% and that of CF$_3$CH$_3$ is 9.6%. 2.7% of ethane and 0.85% of methane are also formed.

EXAMPLE 8

The procedure of Example 7 is followed, the ruthenium-based catalyst being replaced with a catalyst based on iridium deposited in a proportion of 5% on a charcoal of large specific surface area (>900 m$^2$/g).

The following are introduced:

| 5% iridium/charcoal catalyst | 4 g |
|---|---|
| Water | 8 ml |
| TFA | 0.2 mol. |

The reaction is carried out at 150° C. and under a total pressure of 45 bar.

A quantity of gas cover equal to 3 liters.h$^{-1}$ (NTP) is purged continuously, which represents about 30% of the total quantity of hydrogen necessary for the reaction.

The reaction stops after 1 hour.

The degree of conversion of the TFA is 100%. The yield of TFE is 83.5% and that of the trifluoroethane is 16%. 0.35% of methane and 0.25% of ethane are also formed.

EXAMPLE 9

Example 8 is repeated, but at 150° C. and under a total pressure of 10 bar.

The reaction stops after 3 hours.

The degree of conversion of the TFA is 70%.

The yield (Y) of trifluoroethanol (TFE) is 96%. 3.7% of CF$_3$CH$_3$, 0.2% of ethane and 0.1% of CH$_4$ have also been formed.

EXAMPLE 10

The following are introduced into the same reactor as that used in the previous examples:
4 g of a catalyst consisting of 5% of Pt deposited on charcoal having a specific surface area of more than 900 m$^2$/g
8 ml of water
22.8 g of trifluoroacetic acid, i.e. 0.2 mol.

Hydrogenation is carried out at 180° C. and under a total pressure of 40 bar. Some of the gas cover is purged continuously, this corresponding to about 10% of the total quantity of hydrogen necessary to accomplish the reaction.

The reaction stops after 2 hours 45 minutes.

The degree of conversion of the trifluoroacetic acid is 94%. The yield of trifluoroethanol is 96%. The following have also been formed:
2 5% of CF$_3$CH$_3$
1.1% of C$_2$H$_6$
0.4% of CH$_4$.

What is claimed is:

1. A process for the preparation of trifluoroethanol by the hydrogenation of trifluoroacetic acid in the liquid phase, which comprises the steps of:
    reacting hydrogen with trifluoroacetic acid in the liquid phase in a reactor in the presence of a catalyst based on a metal selected from the group consisting of ruthenium, rhodium, iridium and platinum, under a total pressure of between 5 and 50 bar, the ratio of the volume of the liquid phase used in the reactor to the total volume of the reactor being more than about ½; and
    maintaining an absolute partial pressure of hydrogen of more than 1 bar during the reaction.

2. The process of claim 1, wherein the absolute partial pressure of hydrogen is maintained at a value of more than 1 bar by allowing some of the gas phase present in the reactor to escape continuously during the reaction.

3. The process of claim 2, wherein the total pressure is between 5 and 30 bar.

4. The process of claim 2, wherein the ratio of the volume of the liquid phase to the total volume of the reactor is between 0.5 and 0.8.

5. The process of claim 2, wherein the absolute partial pressure of hydrogen is maintained at more than 5 bar.

6. The process of claim 2, wherein the catalyst metal is used in the form of the metal, an oxide or a salt of the metal, or in the form of a mixture thereof.

7. The process of claim 6, wherein the catalyst is deposited on a support selected from the group consisting of charcoal, silica and alumina.

8. The process of claim 2, wherein less than 10% by weight of catalyst is used, expressed as metal relative to the trifluoroacetic acid.

9. The process of claim 1, wherein the total pressure is between 5 and 30 bar.

10. The process of claim 1, wherein the ratio of the volume of the liquid phase to the total volume of the reactor is between 0.5 and 0.8.

11. The process of claim 1, wherein the absolute partial pressure of hydrogen is maintained at more than 5 bar.

12. The process of claim 1, wherein the catalyst metal is used in the form of the metal, an oxide or a salt of the metal, or in the form of a mixture thereof.

13. The process of claim 12, wherein the catalyst is deposited on a support selected from the group consisting of charcoal, silica and alumina.

14. The process of claim 1, wherein less than 10% by weight of catalyst is used, expressed as metal relative to the trifluoroacetic acid.

15. The process of claim 1, wherein the reaction temperature is between 20° and 200° C.

16. The process of claim 15, wherein the reaction temperature is between 70° and 150° C.

17. The process of claim 2, wherein the reaction temperature is between 20° and 200° C.

18. The process of claim 17, wherein the reaction temperature is between 70° and 150° C.

* * * * *